United States Patent [19]
Schiff

[11] Patent Number: 6,080,777
[45] Date of Patent: Jun. 27, 2000

[54] TAXOL AS A RADIATION SENSITIZER

[75] Inventor: Peter B. Schiff, Larchmont, N.Y.

[73] Assignee: The Trustees of Columbia University in the City of New York, New York, N.Y.

[21] Appl. No.: 08/256,963

[22] PCT Filed: Jan. 31, 1992

[86] PCT No.: PCT/US92/00851

§ 371 Date: Dec. 12, 1994

§ 102(e) Date: Dec. 12, 1994

[87] PCT Pub. No.: WO93/14787

PCT Pub. Date: Aug. 5, 1993

[51] Int. Cl.$^7$ ............ A61K 43/00; A01N 43/02
[52] U.S. Cl. ............ 514/449; 424/1.1; 435/366; 435/375
[58] Field of Search ............ 514/449; 424/1.1; 435/366, 375

[56] References Cited

U.S. PATENT DOCUMENTS

| | | | |
|---|---|---|---|
| 4,814,470 | 3/1989 | Colin et al. | 514/449 |
| 4,876,399 | 10/1989 | Holton et al. | 568/817 |
| 4,960,790 | 10/1990 | Stella et al. | 514/449 |
| 5,059,699 | 10/1991 | Kingston et al. | 549/511 |
| 5,157,049 | 10/1992 | Haugwitz et al. | 514/449 |

OTHER PUBLICATIONS

Gupta, Radhey S., "Genetic, Biochemical, and Cross–Resistance Studies with Mutants of Chinese Hamster Ovary Cells Resistant to the Anticancer Drugs, VM–26 and VP16–213." *Cancer Research* (1983) 43: 1568–1574 (Exhibit B).

Choy, H., et al. (1993) "Investigation of taxol as a potential radiation sensitizer." *Cancer* 71: 3774–3778.

Einzig, A.I., et al. (1990) "Phase II study of taxol in patients with advanced ovarian cancer." *Proc. Am. Assoc. Can. Res.* 31: 187 abst. 1114.

Hei, T.K. and Hall, E.J. (1993) "Taxol, radiation, and oncogenic transformation."*Cancer Research* 53: 1368–1372.

Holmes, F.A., et al. (1991) "Phase II trial of taxol, an active drug in the treatment of metastatic breast cancer." *J. Natl. Cancer Inst.* 83: 1797–1805.

Hruban, R.H., et al. (1989) "Taxol toxicity. Epithelial necrosis in the gastrointestinal tract associated with polymerized microtubule accumulation and mitotic arrest." *Cancer* 63: 1944–1950.

Legha, S.S., et al. (1990) "A phase II trial of taxol in metastatic melanoma." *Cancer* 65: 2478–2481.

McGuire, W.P., et al. (1989) "Taxol: A unique antineoplastic agent with significant activity in advanced ovarian epithelial neoplasms." *Ann. Intern. Med.* 111: 273–279.

Rowinsky, E.K., et al. (1990) "Taxol: A novel investigational antimicrotubule agent."*J. Natl. Cancer Inst.* 82: 1247–1259.

Schiff, P.B. and Horowitz, S.B. (1980) "Taxol stabilizes microtubules in mouse fibroblast cells." *Proc. Natl. Acad. Sci. U.S.A.* 77: 1561–1565.

Schiff, P.B., et al. (1979) "Promotion of microtubule assembly in vitro by taxol." *Nature* 227: 665–667.

Sinclair, W.K. (1968) "Cyclic X–ray responses in mammalian cells in vitro." *Radiat. Res.* 33: 620–643.

Sorochinskii, B.V., et al. (1991) "Effects on the self–assembly of cell structures as a factor of modification of radiosensitivity of cells in culture." *Dokl. Akad. Nauk SSSR* 317: 231–233 (Chemical Abstracts 115: 419 abst. 45201a, issued 1991).

Tishler, R.B., et al. (1992) "Taxol: A novel radiation sensitizer." *Intl. J. Radia. Oncol. Biol. Phys.* 22: 613–617.

Tishler, R.B., et al. (1992) "Taxol sensitizes human astrocytoma cells to radiation." *Cancer Research* 52: 3495–3497.

Wani, M.C., et al. (1971) "Plant antitumor agents. VI. The isolation and structure of taxol, a novel antileukemic and antitumor agent from *Taxus brevifolia*." *J. Am. Chem. Soc.* 93: 2325–2327.

Wiernik, P.H., et al. (1987) "Phase I clinical and pharmacokinetic study of taxol." *Cancer Res.* 47: 2486–2493.

Wiernik, P.H., et al. (1987) "Phase I trial of taxol given as a 24–hour infusion every 21 days: Responses observed in metastatic melanoma."*J. Clin. Oncol.* 5: 1232–1239.

*Primary Examiner*—Phyllis G. Spivack
*Attorney, Agent, or Firm*—John P. White; Cooper & Dunham LLP

[57] ABSTRACT

This invention provides a method of increasing sensitivity of cells to the cyctotoxic effects of ionizing radiation which includes incubating the cells with a spindle poison in a suitable carrier at a concentration effective to inhibit the cells from progressing through $G_2$ or M phases of the cell cycle for a time effective to inhibit division of the cells and then administering a cyctotoxic dose of ionizing radiation to the cells.

28 Claims, 6 Drawing Sheets

TAXOL AS A RADIATION SENSITIZER

BACKGROUND OF THE INVENTION

Throughout this application, various publications are referred to within parenthesis. Full bibliographic citations for these references may be found at the end of the specification, immediately preceding the claims. The disclosures for these publications in their entireties are hereby incorporated by reference into this application in order to more fully describe the art to which this invention pertains.

Taxol is the prototype of a new class of antineoplastic agents that targets microtubules. It is a natural product isolated from the bark of the western yew, *Taxus brevifolia*. Its structure, a novel diterpene compound, and antitumor activity in rodents were reported in 1971 (16). The drug's unique mechanism of action has generated considerable interest, both for its use to probe the function of the cytoskeleton in basic science, and as a chemotherapeutic agent in oncology. Taxol is known to be a potent cytotoxic agent against a range of human malignancies using cell culture and xenographic model systems (9). Human studies have demonstrated taxol's ability to increase the mitotic index in a variety of tissues (4). Clinical trials have demonstrated that taxol is an active agent in salvage treatment for epithelial ovarian malignancies (2, 5, 15) and has activity against breast cancer (3) as well as melanoma (7, 18).

Unlike agents that bind to tubulin, the subunit of microtubules, and inhibit microtubule formation (vinca alkaloids, podophyllotoxin, and colchicine), taxol induces in vitro formation of exceptionally stable microtubules (10). Tissue and culture studies have shown the ability of taxol to block and/or prolong cells in the G2 or M phase of the cell cycle (11). The microtubule cytoskeletons of taxol-treated cells are exceedingly stable to depolymerization, as are isolated drug-treated microtubules. In addition, electron microscopy reveals an abnormal microtubular cytoskeleton in drug-treated cells. The inability of these cells to pass through the G2 and M phases of the cell cycle probably results from the inability of these cells to form a competent mitotic spindle or to disassociate a drug-treated spindle. Taxol additionally blocks the migration behavior of cells in culture. These observations may explain the observed antitumor activity of the drug.

Taxol has undergone several Phase I trials at many institutions (9). Plasma concentrations of 1 nM to 5 μM taxol at safe therapeutic doses are comparable to those required for the antiproliferative and microtubule-stabilizing effects of the drug in vitro. Mitotic arrest has been observed in the esophagus, stomach, small intestine, colon, liver, skin, bone marrow, and testes of patients biopsied within 11 days after receiving taxol (4). Dose-limiting toxicity includes leukopenia, thrombocytopenia, alopecia, nausea and vomiting, diarrhea, stomatitis, peripheral neuropathy, rashes, elevated serum triglyceride levels, and severe hypersensitivity (most likely related to the cremophor vehicle) (1, 5, 6, 17, 18). Partial responses have been reported in patients with non-small cell lung cancer, melanoma, and ovarian cancer. One Phase II study has reported significant activity against standard drug protocol refractory ovarian cancer (8).

It is well known from radiobiological principles that G2/M is the most radiosensitive phase of the cell cycle (13). However, use of taxol, related compounds or pharmaceutically acceptable salts thereof to enhance the cytotoxic effect of ionizing radiation has not previously been described.

SUMMARY OF THE INVENTION

This invention provides a method of increasing the sensitivity of cells to the cytotoxic effects of ionizing radiation which comprises first incubating the cells with a spindle poison in a suitable carrier at a concentration effective to inhibit the cells from progressing through the G2 or M phases of the cell cycle for an amount of time effective to inhibit division of the cells and then administering an effective cytotoxic dose of ionizing radiation to the cells.

This invention also provides a method of treating a cancer patient which comprises first administering to the patient a spindle poison in a suitable carrier in an amount effective to inhibit tumor cells in the patient from progressing through the G2 or M phases of the cell cycle for an amount of time effective to inhibit division of the tumor cells and then administering an effective cytotoxic dose of ionizing radiation to the patient.

This invention further provides a method of increasing the sensitivity of cells to the cytotoxic effects of bleomycin which comprises first incubating the cells with a spindle poison in a suitable carrier at a concentration effective to inhibit the progression of the cells through the G2 or M phases of the cell cycle for an amount of time effective to inhibit cell division and then exposing the cells to an effective cytotoxic concentration of bleomycin.

This invention still further provides a kit useful for treating a cancer patient which comprises a spindle poison in an amount sufficient to establish a concentration of the poison in the body of the patient effective to inhibit the progression of tumor cells through the G2 and M phases of the cell cycle and an effective cytotoxic dose of a radioisotope in aqueous solution, an antibody-conjugated radioisotope or bleomycin.

Figure 1:
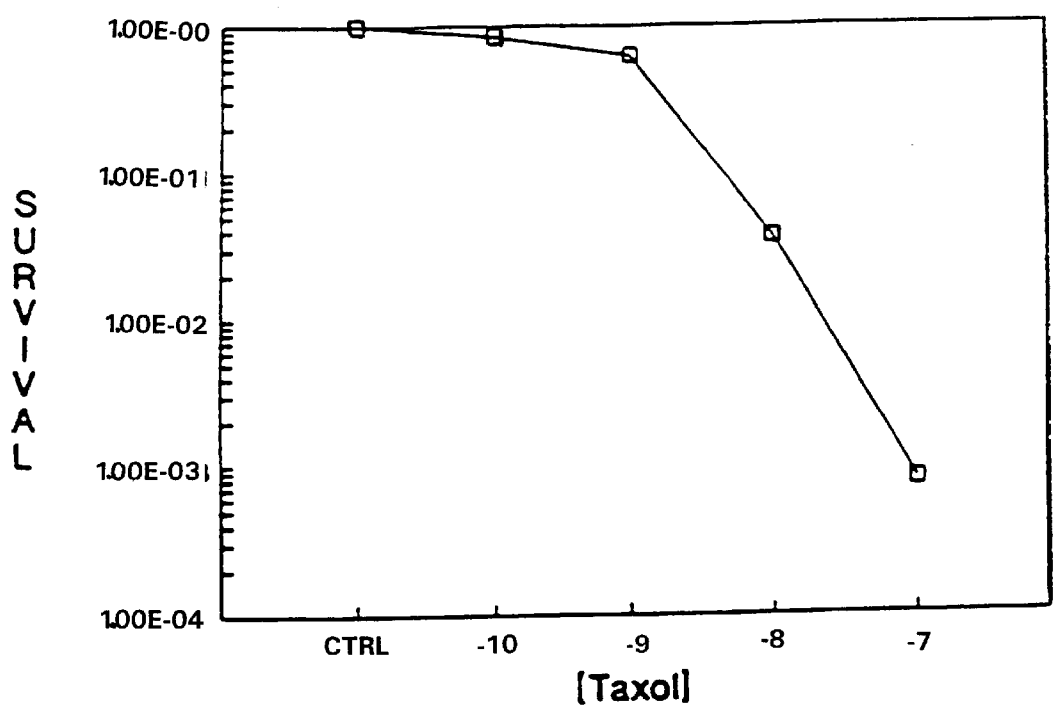
FIG. 1 Cell surviving fraction versus drug concentration following a 24 hr treatment of human astrocytoma cells with taxol. Control plating efficiencies ranged from 52 to 61%. Standard error bars are shown when greater than the size of the symbols.
Figure 2A:
FIG. 2 Nomarski-interference contrast photomicrographs of human astrocytoma cells following a 24 hr treatment with various concentrations of taxol: (a) 0 nM; (b) 1 nM, (c) 10 nM; and (d) 100 nM. The effect of the drug on cellular morphology is apparent as is nuclear multi-micronucleation at the higher concentrations. Calls progressively accumulate at the G2/M phase of the cell cycle.
Figure 2B:
Figure 2C:
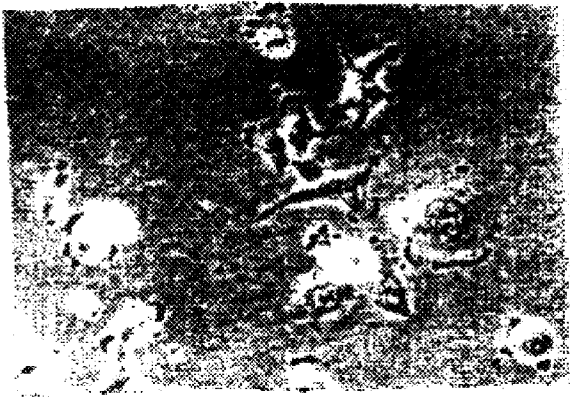
Figure 2D:
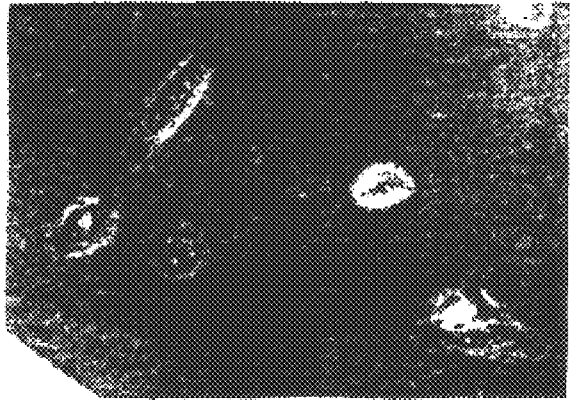

B. Survival of cells treated with 10 nM taxol and 6 Gy of radiation. Survival of irradiated cells is expressed relative to unirradiated cells treated with taxol for the same period of time. Therefore, the change in cell survival seen as a function of time of taxol exposure is a measure of the increased interaction between these two treatments. A relative decrease in cell survival, and therefore an increase in the level of interaction between taxol and radiation is seen for cells treated for 16 and 24 hours. C. Percent of cells in the G2 or M phases of the cell cycle as determined by flow cytometry for the times indicated.

DETAILED DESCRIPTION OF THE INVENTION

This invention provides a method of increasing the sensitivity of cells to the cytotoxic effects of ionizing radiation which comprises first incubating the cells with a spindle poison in a suitable carrier at a concentration effective to inhibit the cells from progressing through the G2 or M phases of the cell cycle for an amount of time effective to inhibit division of the cells and then administering an effective cytotoxic dose of ionizing radiation to the cells.

Suitable cells for use in accordance with the practice of this invention may be tumor cells. The tumor cells may be brain tumor cells, e.g., astrocytoma, glioblastoma multiforms or medulloblastoma cells. The tumor cells may also be ovarian tumor cells, e.g., epithelial, sex-chord stromal, lipid, germ or gonadoblastoma cells. The tumor cells may further be lung tumor cells, e.g., adenocarcinoma, large cell, small cell or squamous cell tumor cells. The tumor cells may still further be breast tumor cells, e.g., invasive duct carcinoma, medullary carcinoma or muscinous carcinoma cells. The tumor cells may also be melanoma cells.

The term "spindle poison" as used herein means any agent capable of interfering with the functioning of the microtubules in a cell with the result that cell division is inhibited and the cell is blocked in the G2 or M phases of the cell cycle. Spindle poisons may be agents which interfere with microtubule formation and thereby inhibit cell division, e.g., vinblastin and vincristin. Spindle poisons may also be agents which stabilize microtubules and prevent their disassembly during cell division. Examples of such microtubule-stabilizing agents suitable for use in the practice of this invention include taxol-related compounds. The term "taxol-related compound" as used herein encompasses compounds possessing a microtubule-stabilizing activity similar to taxol. In the presently preferred embodiment of this invention, the taxol-related compound is taxol. Taxol may be a natural product from the bark of the yew Taxus Sp. L. one species of this genus useful as a source of taxol in the practice of this invention is the yew *Taxus brevifolia*. However, the term "taxol" as used herein encompasses not only taxol from this source, but taxol produced by any method, including chemical synthesis or tissue culture production.

Suitable carriers for a spindle poison may be any of a number of aqueous solutions well known to those skilled in the art. Presently preferred are aqueous solutions of dimethyl sulfoxide.

For the purposes of this invention, an "effective inhibiting concentration" of the spindle poison is any concentration of the spindle poison effective to inhibit the progression of the cells through the cell cycle and cause cells to accumulate in the G2 or M phases. Typically, the effective inhibiting concentration of the spindle poison is a concentration from about 1 nM to about 50 μM.

In the practice of this invention, an "effective inhibiting amount of time" is any amount of time for which incubation of the cells with the spindle poison at an effective inhibiting concentration will be effective to inhibit the progression of cells through the G2 or M phases of the cell cycle. Typically, the effective inhibiting amount of time is an amount from about 6 hours to about 24 hours, desirably an amount from about 8 hours to about 20 hours. More desirably, the effective inhibiting amount of time is an amount about 18 hours.

In one embodiment of this invention, administration of an effective cytotoxic dose of ionizing radiation to the cells comprises exposing the cells to a beam of ionizing radiation. For the purposes of this invention, an effective cytotoxic dose of ionizing radiation is any dose of ionizing radiation effective to kill cells. Typically, the effective cytotoxic dose of ionizing radiation is a dose from about 1 Gy to about 10 Gy, desirably a dose from about 2 Gy to about 8 Gy. Methods of producing a beam of ionizing radiation suitable for the exposure of cells in accordance with the practice of this invention are well known to those skilled in the art. In the presently preferred embodiment of this invention, the beam of radiation is produced by an irradiator. The term "irradiator" as used herein is intended to mean a device comprising a lead shield surrounding a radioisotope which emits ionizing radiation and a mechanism for exposing cells placed adjacent to the irradiator to the ionizing radiation. Methods of using an irradiator to expose cells to ionizing radiation are well known to those skilled in the art. In the practice of this invention, the irradiator may comprise the radioisotope Cesium-137 or the radioisotope Iridium-192.

In another embodiment of this invention, the administration of an effective cytotoxic dose of ionizing radiation to the cells comprises contacting the cells with an aqueous solution containing a radioisotope. For the purposes of this invention, an "effective cytotoxic dose" of ionizing radiation is any dose of ionizing radiation effective to kill cells. Typically, the effective cytotoxic dose of ionizing radiation is a dose from about 1 Gy to about 10 Gy, desirably a dose from about 2 Gy to about 8 Gy. Suitable radioisotopes for use in accordance with the practice of this invention may be any of a number of radioisotopes well known to those skill in the art. In the presently preferred embodiment of this invention, the radioisotope is Phosphorous-32.

This invention also provides a method of treating a cancer patient which comprises first administering to the patient a spindle poison in a suitable carrier in an amount effective to inhibit tumor cells in the patient from progressing through the G2 or M phases of the cell cycle for an amount of time effective to inhibit division of the tumor cells and then administering an effective cytotoxic dose of ionizing radiation to the patient. Administration of a spindle poison to a patient may be by any of the means well known to those skilled in the art suitable for contacting cells in the body of a patient with a spindle poison, e.g., by intravenous injection. Preferably, the patient is a human patient.

As stated above, the term "spindle poison" as used herein encompasses any agent capable of interfering with the functioning of the microtubules in a cell with the result that cell division is inhibited and the cell is blocked in the G2 or M phases of the cell cycle. The spindle poison may be an agent which stabilizes microtubules, e.g., a taxol-related compound. In one embodiment of this invention, the taxol-related compound is taxol. Taxol may be a natural product of the yew Taxus Sp. L. However, the term "taxol" as used herein encompasses taxol produced by any method, including chemical synthesis or tissue culture production.

Suitable carriers for administering a spindle poison to a patient may be any of a number of aqueous infusion solutions well known to those skilled in the art. Presently preferred is an aqueous infusion solution comprising 5% dextrose injection USP, i.e., D5W.

In the practice of this invention, the amount of the spindle poison effective to inhibit the progression of cells through the G2 or M phases of the cell cycle is an amount of the spindle poison sufficient to establish a concentration of the agent in the blood of the patient effective to inhibit the cells from progressing through the G2 or M phases of the cell cycle. For the purposes of this invention, "an effective inhibiting concentration" of a spindle poison is any amount of the poison effective to inhibit the progression of cells through the G2 or N phases of the cell cycle. Typically, the effective inhibiting concentration of the spindle poison is a concentration from about 1 nM to about 50 $\mu$M. The effective concentration of the spindle poison in the blood of the animal may be maintained by readministering the poison to the patient at an interval of time after the preceding administration. Methods of determining the appropriate length of the interval between administrations of the spindle poison are well known to those skilled in the art. Presently preferred is an interval of about one week between administrations.

For the purposes of this invention, an amount of time effective to inhibit the progression of cells through the G2 or M phases of the cell cycle is any amount of time for which incubation of the cells with a spindle poison will be effective to inhibit the progression of cells through the cell cycle and cause the cells to accumulate in the G2 or M phases. Typically, the "effective inhibiting amount" of time is an amount greater than about 24 hours.

In one embodiment of this invention, the effective cytotoxic dose of ionizing radiation is administered by exposing the patient to a beam of radiation produced by a linear accelerator. For the purposes of this invention, an "effective cytotoxic dose" of ionizing radiation is any dose of ionizing radiation effective to kill-cells. Typically, the effective cytotoxic dose of ionizing radiation absorbed by a patient from exposure to a beam of radiation in accordance with the practice of this invention is a dose from about 4,000 cGy to about 8,000 cGy. Desirably, the effective cytotoxic dose of ionizing radiation is a dose from about 6,500 cGy to about 7,500 cGy. In the practice of this invention, the effective cytotoxic dose of ionizing radiation may be administered to the patient in a schedule of increments. Methods of establishing a schedule of increments for administering ionizing radiation to a patient are well known to those skilled in the art. An example of such a schedule contemplated by this invention comprises a dose of ionizing radiation of about 200 cGy per day for five days per week for a period from about six weeks to about eight weeks.

In another embodiment of this invention, an effective cytotoxic dose of ionizing radiation is administered by implanting a radioisotope in tumors in the body of the patient for an amount of time sufficient to expose the tumor to the effective cytotoxic dose. For the purposes of this invention, an "effective cytotoxic dose" of ionizing radiation is any dose of ionizing radiation effective to kill cells. Typically, the effective cytotoxic dose of ionizing radiation is a dose from about 8,000 cGy to about 20,000 cGy. Desirably, the effective cytotoxic dose is a dose about 16,000 cGy. Suitable radioisotopes for implanting in tumors in the body of a patient in accordance with the practice of this invention may be any of those well known to those skilled in the art. Presently preferred are Iodine-125 or Iridium-192.

The practice of this invention also contemplates exposing the patient to a beam of ionizing radiation. Methods of generating a beam of ionizing radiation suitable for application to a patient are well known to those skilled in the art. In the presently preferred embodiment of this invention, the radiation beam is generated by a linear accelerator. One skilled in the art would be readily able to determine without undue experimentation whether the beam of radiation is to be applied to the patient before or after the radioisotope is implanted. Typically, the effective cytotoxic dose of ionizing radiation to which the patient is exposed in accordance with the practice of this invention comprises a dose of ionizing radiation from about 4,000 cGy to about 6,000 cGy administered by the beam of radiation and a dose of ionizing radiation from about 2,000 cGy to about 4,000 cGy administered by the radioisotope implant.

In a further embodiment of this invention, the effective cytotoxic dose of ionizing radiation is administered to the patient by radiosurgery. The term "radiosurgery" as used herein is intended to mean a procedure for applying a dose of ionizing radiation to a narrowly defined area of tissue in the body of the patient while avoiding exposing surrounding tissue. Radiosurgery allows for the accurate determination of target size and location, treatment planning and accurate delivery of radiation. A radiosurgery system includes a stereotactic frame, an appropriate radiation source and computer hardware and software. The appropriate radiation source may be a "gamma-knife", e.g., a gamma knife containing Cobalt-60, or a linear accelerator. Typically, the dose of ionizing radiation a patient is exposed to by radiosurgery is a dose from about 1,200 cGy to about 2,800 cGy.

This invention further provides a method of increasing the sensitivity of cells to the cytotoxic effects of bleomycin which comprises first incubating the cells with a spindle poison in a suitable carrier at a concentration effective to inhibit the progression of the cells through the G2 or M phases of the cell cycle for an amount of time effective to inhibit cell division and then exposing the cells to an effective cytotoxic concentration of bleomycin. For the purposes of this invention, an "effective cytotoxic concentration of bleomycin" is any concentration of bleomycin effective to kill cells. Methods of determining effective cytotoxic concentrations of bleomycin are well known to those skilled in the art or are readily determinable by routine experimentation.

This invention still further provides a kit useful for treating a cancer patient which comprises a spindle poison in an amount sufficient to establish a concentration of the poison in the body of the patient effective to inhibit the progression of tumor cells through the G2 and M phases of the cell cycle and an effective cytotoxic dose of a radioisotope in aqueous solution, an antibody-conjugated radioisotope or bleomycin. The kit of this invention may include instructions for administering the spindle poison and the aqueous solution of the radioisotope, the antibody-conjugated radioisotope or bleomycin in accordance with the practice of this invention.

This invention will be better understood from the Results and Discussion which follow. However, those skilled in the art will readily appreciate that the specific results discussed are only illustrative of the invention as described more fully in the claims which follow thereafter.

Materials and Methods

The astrocytoma cell line (G18) was established in culture from a surgical specimen obtained from the Neurological Institute of New York, Columbia-Presbyterian Medical Center (12). Cells were grown in Modified Eagles Medium (MEM) with Hanks Balanced Salts (HBS, obtained from Gibco) and 10% Fetal Calf Serum (Hyclone) with 12.5 ml SerXtend (Hana Biological) per 500 ml of serum. Medium was supplemented with MEM L-glutamine, essential amino acids, non-essential amino acids, vitamins, and gentamicin. For survival curve incubations, the medium was supplemented with penicillin/streptomycin. Cells were routinely grown in flasks with loosely capped tops, in incubators with 5% $CO_2$ and subcultured 1–2 times per week at a ratio of 1:20 (12).

Taxol (NSC 125973) was obtained from the NCI drug program. A stock solution of $10^{-2}$ M was prepared in dimethyl sulfoxide (DMSO), kept at −40° C. and thawed for use. The quantity of drug and DMSO added per dish was between 0.1%–1.0% of the total volume of medium.

Cells were incubated in slide flasks. Approximately $2 \times 10^4$ cells and 2 ml of medium were added to each flask. These were allowed to incubate for approximately 24 hr prior to removal of the medium and photography. Nomarski interference contrast photomicrography was carried out using an Olympus Vanox AH4 microscope.

Cells were acutely irradiated with a $^{137}Cs$ irradiator (Atomic Energy of Canada Model GC40) operating at a dose rate of 1.12 Gy/min. Irradiation times ranged from 1.8 to 7.1 minutes.

Cells were plated in 100 mm dishes with 10 ml of medium and allowed to attach for approximately 20 hr. The number of cells per dish was chosen such that 100–200 colonies would survive after a specified treatment. Taxol or DKSO was then added and the cells allowed to incubate for another 20–24 hr with drug present. Following the incubation period, cells were acutely irradiated, medium removed by aspiration, and 10 ml of medium was added back. Samples with unirradiated controls were also prepared in the same way. Dishes were then incubated for 10 days. Three plates were prepared for each concentration and dose of irradiation. Cells were fixed in 75% methanol/25% acetic acid and stained with crystal violet. Colonies were considered to be a collection of 50 or more cells and were counted on a per dish basis. Survival was determined from the number of cells per dish, normalized by unirradiated controls treated with the same concentration of taxol or DNSO.

Cells were irradiated with 6 Gy of $^{137}$ gamma rays at 0, 8, and 24 hr after addition of 10 nM taxol. At each of the time points noted above, cells were additionally prepared for flow cytometry as follows: the medium was aspirated, cells washed with HBS, then trypsinized and washed in normal medium. Cells were rewashed and then resuspended in cold methanol and refrigerated. Cells were resuspended in 50 µg/ml propidium iodide prior to flow cytometry using a Coulter dual laser EPICS 752. Flow studies measured the number of cells versus DNA content and allowed for the determination of the fraction of cells in each phase of the cell cycle. Cells were also studied (a) after exposure to a range of concentrations and (b) as a function of length of exposure to 10 nM taxol.

Results and Discussions

The cytotoxic effect on the human astrocytoma cell line G18 of a range of concentrations of taxol are shown in FIG. 1. At 1 nM, and for a 24-hour exposure, there is no significant difference from the control, while after a 100 nM treatment, about 0.1% of cells retain clonogenic potential relative to controls.

The morphological consequences of 24-hour taxol exposures on these astrocytoma cells are shown in FIG. 2. Cells were photographed 24 hours after taxol addition and even at 1 nM (FIG. 2, b), there is a clear change in cellular morphology, with cells being unable to spread. They have lost polarity, yet show little evidence of nuclear anomalies. At 10 nM (FIG. 2, c), there are clear changes in nuclear morphology, with many cells showing nuclei fragmented into numerous micronuclei. These may represent abortive attempts at division, and hence, cells will accumulate with a G2/M DNA content. This situation is dramatically enhanced following a 100 nM treatment (FIG. 2, d), where there are clearly considerably fewer cells, an overall flattening of cells, and with the vast majority of cells showing a multi-micronucleate phenotype.

Overall, this microtubule stabilizing agent has a dose dependent effect on cellular behavior, consistent initially with a breakdown of cytoskeletal function and hence cellular shape and mobility, and then accumulation of cells in late G2/M. The inability of cells to erect functioning spindles then results in either the reformation of nuclear membranes around groups of chromosomes (multi-micronucleation), or else, the nuclear membrane breaks down only partially and then reforms in clusters. The results would then be expected to be a time- and concentration-dependent increase in the proportion of cells with a G2 DNA content and accumulation in the G2/M phases of the cell cycle. This was confirmed in the astrocytoma cell line by flow cytometric analysis of cellular DNA contents. The fraction of cells at different stages of the cell cycle following treatment with 10 nM taxol is shown in Table 1.

TABLE 1

FLOW CYTOMETRY OF HUMAN ASTROCYTOMA CELLS INCUBATED WITH 10 nM TAXOL AT VARIOUS TIME INTERVALS

| Treatment | Time (hrs.) | G1(%*) | S(%) | G2/M(%) |
| --- | --- | --- | --- | --- |
| Control | 0 | 58.1 | 25.3 | 16.6 |
|  | 24 | 56.6 | 23.9 | 19.5 |
| 10 nM taxol | 2 | 54.1 | 27.7 | 18.2 |
|  | 8 | 16.6 | 32.4 | 51.0 |
|  | 24 | 0.0 | 3.5 | 96.5 |

*% = Percentage of cells in different stages of the cell cycle.

After two hours of treatment with 10 nM taxol, there is no significant difference from the control distributions. However, at eight hours there is a clear change in the proportion of cells in each of the phases, with a diminution of cells in G1 phase and an augmentation of cells in G2/M (to approximately 50%). By 24 hours, cellular DNA contents are consistent with the vast majority of cells (96.5%) having progressed through the cell cycle and accumulated with G2/M DNA contents. That is, cells cannot complete a successful mitosis. The flow cytometric data and cellular observations complement each other and indicate that even following taxol removal, the micronucleated state of cells is incompatible with continued proliferative potential.

Figure 3A:
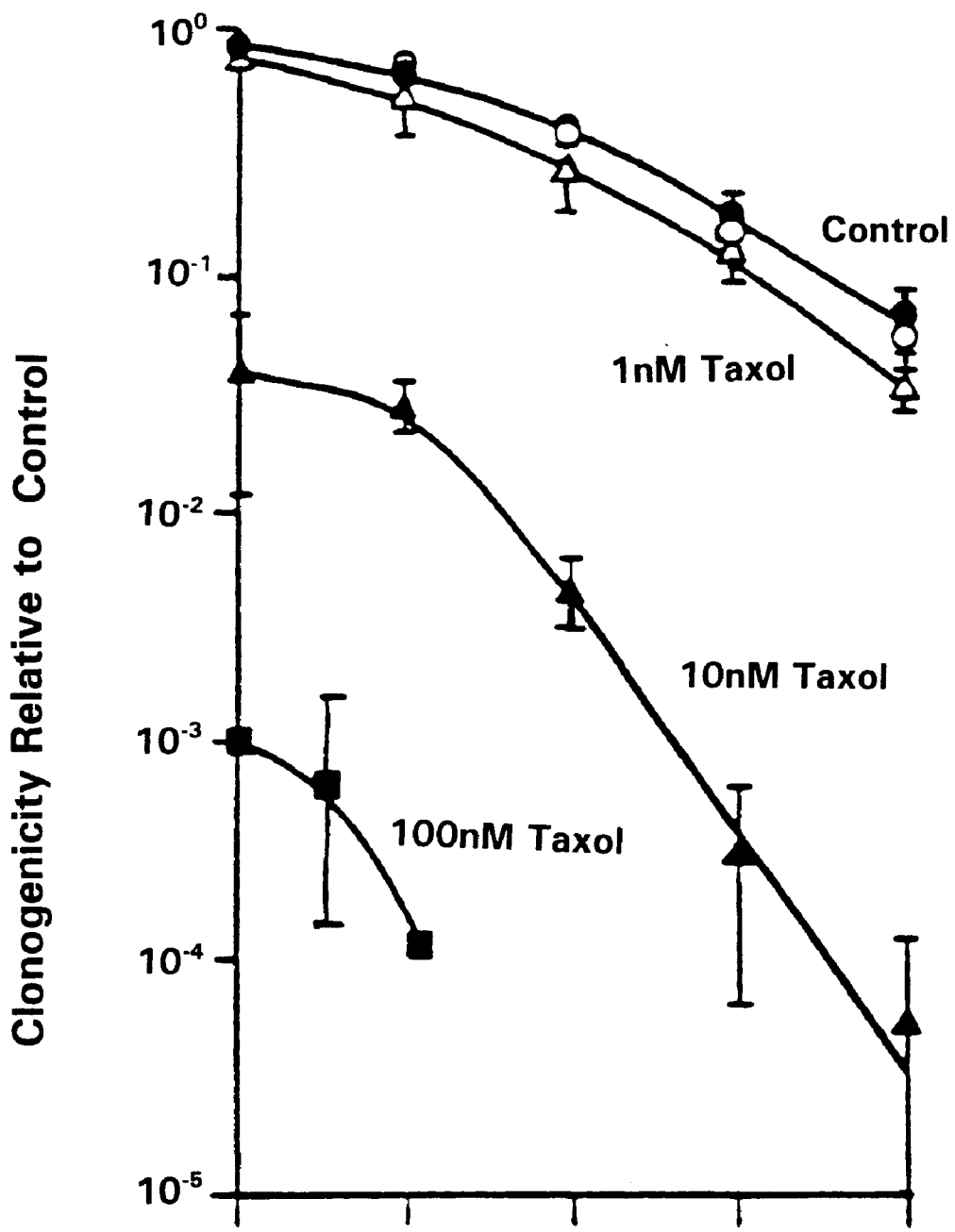
FIG. 3 Radiation survival curves with different concentrations of taxol. Clonogenicity for G18 cells is expressed as a function of taxol concentration and radiation dose. A. Survival is expressed on an absolute scale, relative to unirradiated controls without taxol. The effect of taxol alone on cell survival can be seen as the change in survival at 0 Gy. The interaction of taxol and radiation on cells is demonstrated by the change in the shape of the curves at higher taxol concentrations. B. Survival curves are presented with survival at a particular radiation dose expressed relative to unirradiated controls with the same concentration of taxol. This emphasizes the change in the shape of the survival curves.

While recognizing that taxol alone is a potent cytotoxic agent, the time and concentration dependence in the proportion of cells in the late G2/M phase of the cell cycle is exploitable by the use of ionizing irradiations. The rationale for combining ionizing radiation and taxol therapeutically is that cells in G2 or M are relatively more radiosensitive than cells in other phases of the cell cycle. Clonogenicity results for 24-hour treatments with different concentrations of taxol alone, radiation alone and combined treatments of taxol and radiation at twenty four hours are shown in FIG. 3A. Control plating efficiencies during the course of these experiments ranged from 53–72%. It can readily be seen that taxol alone is dose-dependently cytotoxic, with less than 0.1% clonogenic capacity at 100 nM, about 5% at 10 nM and about 90% at 1 nM. Constant treatment with taxol (i.e., for the 10 day cell incubation period) again resulted in about 90% clonogenicity at 1 nM but less than 0.01% clonogenicity at 10 nM, indicating a time- and concentration-dependent cytotoxicity.

Figure 3B:
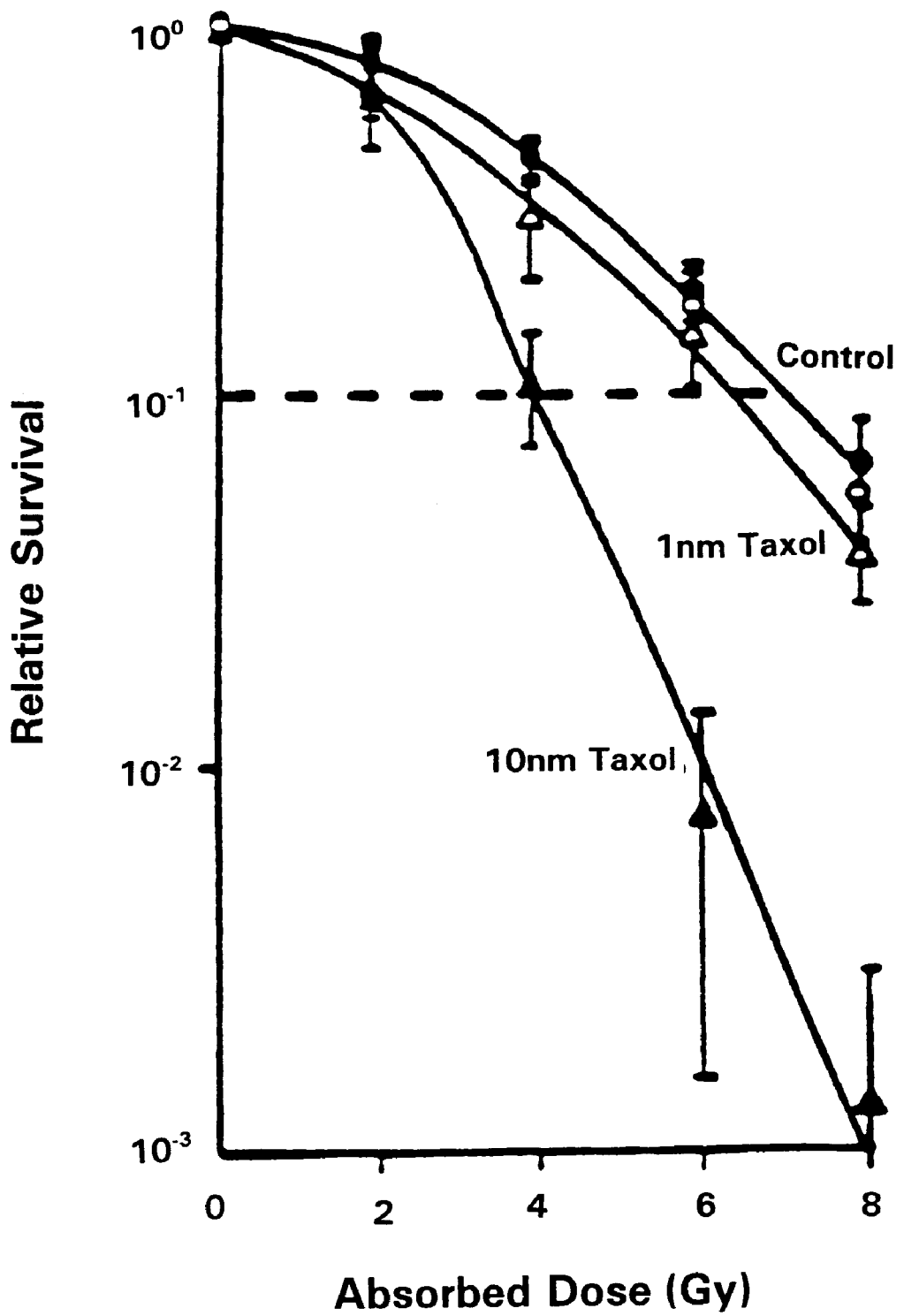

The relative increase in radiosensitivity is demonstrated by the change in the shape of the survival curves at higher taxol concentrations. This change is more clearly demonstrated in FIG. 3B, where the survival curves are normalized by the plating efficiencies of cells treated with the same taxol concentration and without radiation, i.e., survival for taxol alone is defined as 100% for each of these curves. The relative decrease in survival for a given radiation dose is apparent. There was an 87% relative survival after 2 Gy alone, which is compatible with that expected from this comparatively radio-resistant astrocytoma cell line. In the presence of 10 nM taxol, relative survival declined to 61%, and as radiation doses increase, there is an enhanced decrease in the surviving fraction for the combined treatment, reaching a factor of 54 at a dose of 8 Gy (5%) versus 8 Gy plus 10 nM taxol (0.093%, data not shown in the Figure).

Combined treatment studies indicate that radiation is relatively more cytotoxic as the concentration of taxol is increased (see FIG. 3). The enhancement of the response to radiation by taxol, based on the cell cycle principles discussed above, is seen in the concentration range where kinetic and cell cycle effects were observed. For purposes of the future use of the combination of these two modalities, their interaction can be viewed in two ways. At the higher taxol concentration of 10 nM, the drug itself demonstrates a significant degree of cytotoxicity. In this case, the interaction could be viewed as an interaction between a chemotherapeutic agent and radiation. For concentrations in the 1 nM range, there is no significant cell death without the radiation, but there is the suggestion of increased cytotoxicity for a given dose of radiation. Taxol would be classified as a radiosensitizer when employed at this concentration (15). The sensitizer enhancement ratio (SER) at 10% survival for 10 nM taxol was approximately 1.8 and for 1 nM taxol the SER was approximately 1.2.

Figure 4A:
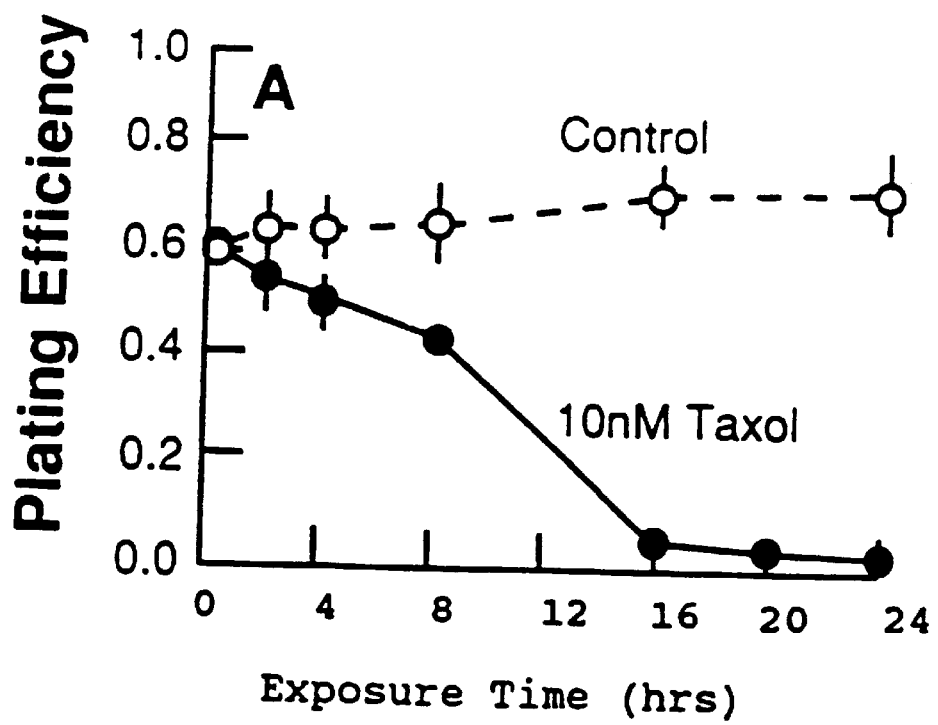
FIG. 4 Cytotoxicity and enhancement of radiation sensitization as a function of time of exposure to 10 nM taxol. Cells were exposed to 10 nM taxol for the indicated time periods and clonogenicity assessed with and without 6 Gy irradiation. A. Plating efficiency, or effect of taxol alone on cell survival. For DMSO-treated controls, the plating efficiency is roughly stable, perhaps increasing slightly as a function of time, whereas for the taxol-treated cells, there is clearly a decrease in plating efficiency as a function of time.
Figure 4B:
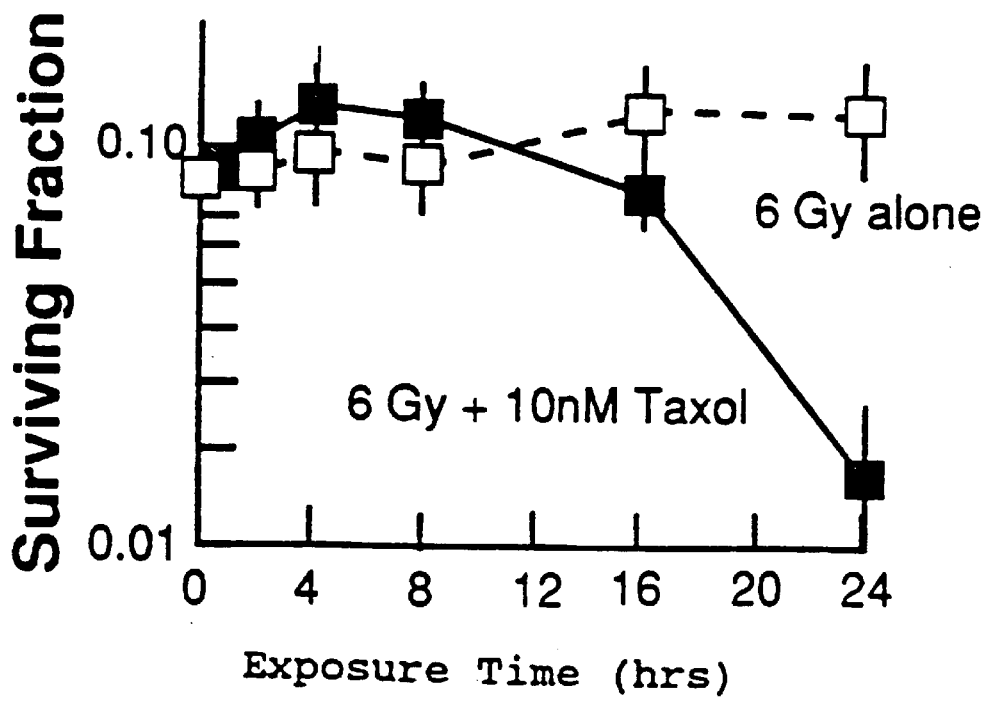
Figure 4C:
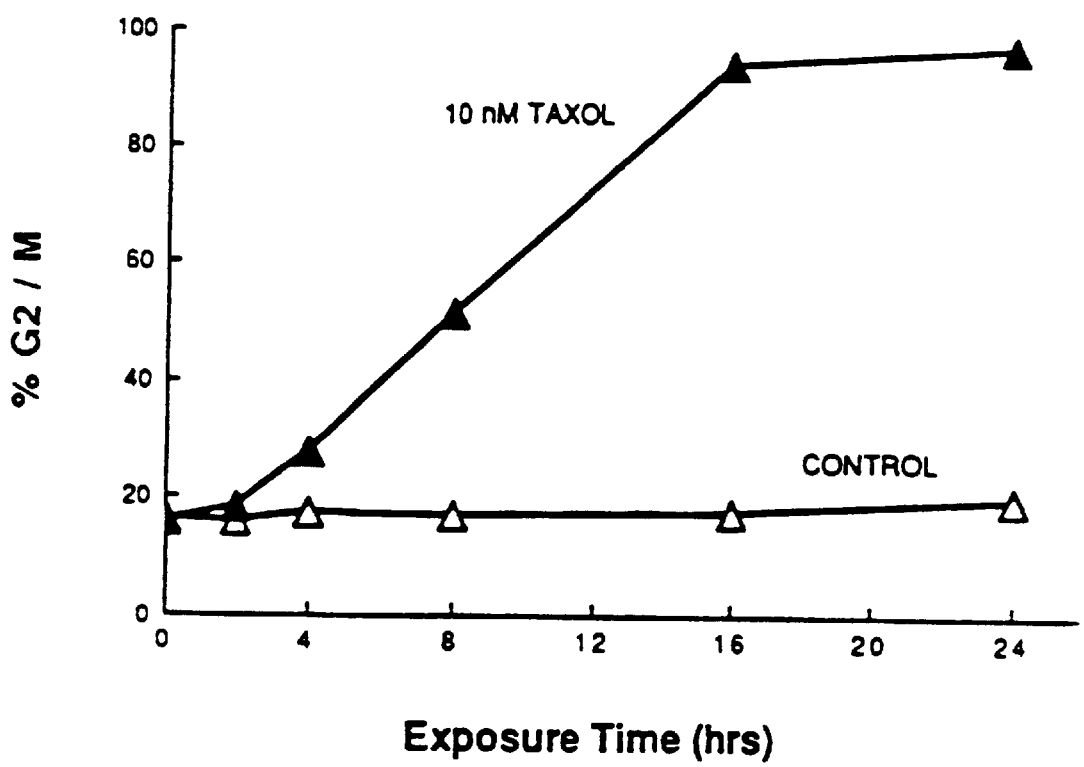

Experimental data supporting the proposed mechanism of interaction between taxol and radiation are shown in FIG. 4. The longer cells are exposed to 10 nM taxol, the more cells accumulate in the G2 or M phases of the cell cycle (8), as shown in FIG. 4C and Table 1. Plating efficiency decreases as the incubation time with 10 nM taxol increases (see FIG. 4A). As the number of cells in G2 or M increases, the relative sensitivity of the cell population to radiation also increases. FIG. 4B shows the time-dependent increase in cell sensitivity to radiation, which is similar to the time-dependent sensitivity to cytotoxicity (see FIG. 4A). It is important to note that survival as shown in FIG. 4B is expressed relative to unirradiated controls exposed to taxol for the same length of time (i.e., the data presented in FIG. 4A). Thus, these data represent the relative increase in the interaction between taxol and irradiation. The interaction between taxol and radiation therefore depends on the cell cycle distribution of cells and is not a result of direct interaction between the two modalities.

Clearly then, a 24-hour treatment with 10 nM taxol results in a dramatic enhancement in the fraction of cells becoming clonogenically incompetent. As is obvious from the flow cytometric analysis of DNA contents (see Table 1), the majority of cells irradiated following the 24-hour taxol treatment are accumulated in the G2/M cycle phases. The enhanced level of cell kill is then consistent (at least in part) with the greater radiosensitivity of G2/M cells. To demonstrate that this effect depends on the distribution of cells in the cell cycle, cells were irradiated with 6 Gy after 10 nM taxol treatment for 2, 8 and 24 hours. No significant difference was seen between 6 Gy and taxol at 2 and 8 hours (9–14% relative survival). However, the results of FIG. 3 were confined to the 24 hour time point, namely 14% relative clonogenicity after 6 Gy and 0.14% relative cell clonogenicity for the 24-hour taxol-treated cells irradiated with 6 Gy. Mote that the results obtained at 8 hours were for cells where there is a significant depletion of G1 cells and enhancement of G2 calls (see Table 1), but at this time, accumulations and/or cellular modifications are inadequate to demonstrate differences in radiation sensitivity.

Conclusions

The results obtained with cycling, aerated, radio-resistant brain tumor cells indicate that significant advantage may derive from appropriate time-concentration dependent interactions in combined modality protocols. A role for radiation therapy and taxol, particularly in those tumors where taxol alone shows some promise, is thereby worthy of consideration. The combination may also be useful in the treatment of refractory brain tumors, since normal tissue is quiescent. This difference in cellular behavior should result in a therapeutic gain for combined treatment.

The potential for the combination of taxol and radiation being clinically useful is based on a number of factors. The experiments presented here were performed at clinically achievable drug concentrations (10 nM or less). Clinical trials have shown that drug concentrations of 200 nM can be maintained for greater than thirty hours using a 6 hour infusion of 230 mg per $m^2$ taxol (12). Peak concentrations of roughly 4000 nM were achieved. Regimens of this type have been used with acceptable levels of taxol-related toxicity.

References

1. Donehower, R. K. et al. Phase I trial of taxol in patients with advanced cancer. Cancer Treat Rep. 71:1171; 1987.
2. Einzig, A. I. et al. Phase II Study of Taxol in Patients With Advanced Ovarian Cancer. Proc. Am. Assoc. Can. Res. 31:1114; 1990.
3. Holmes, F. A. et al. Phase II trial of taxol, an active drug in the treatment of metastatic breast cancer. JNCI 83:1797; 1991.
4. Hruban, R. H. et al. Taxol toxicity. Epithelial necrosis in the gastrointestinal tract associated with polymerized microtubule accumulation and mitotic arrest. Cancer 63:1944; 1989.
5. Kris, M. G. et al. Phase I trial of taxol given as a 3-hour infusion every 21 days. Cancer Treat. Rep. 70:605; 1986.
6. Legha, S. S. et al. Phase I study of taxol using a 5-day intermittent schedule. J. Clin. Oncol. 4:762; 1986.
7. Legha, S. S. et al. A phase II study of taxol in metastic melanoma. Cancer 65:2478; 1990.
8. McGuire, W. P. et al. Taxol: a unique antineoplastic agent with significant activity in advanced ovarian epithelial neoplasms. Ann. Intern. Med. 111:273; 1989.
9. Rowinsky, E. K. et al. Taxol: a novel investigational antimicrotubule agent. JNCI 82:1247; 1990.
10. Schiff, P. B. et al. Promotion of microtubule assembly in vitro by taxol. Nature (London) 277:665; 1979.
11. Schiff, P. B. et al. Taxol stabilizes microtubules in mouse fibroblast cells. Proc. Natl. Acad. Sci. 77:1561; 1980.
12. Schultz, C. J. et al. Radioresponse of human astrocytic tumors across grade as a function of acute and chronic irradiation. Int. T. Radiat. Oncol. Biol. Phys. 19:1397; 1990.

13. Sinclair, W. K. Cyclic X-ray responses in mammalian cells in vitro. Radiat. Res. 33:620; 1968.
14. Steel, G. G. Terminology in the description of grug-radiation interaction. Int. J. Radiat. Onc. Biol. Phys. 5:1145; 1979.
15. Thigpen, T. T. et al. Phase II trial of taxol as second-line therapy for ovarian carcinoma: a gynecological group study. Proc. Am. Soc. Clin. Oncol. 9:604, 1990.
16. Wani, M. C. et al. Plant antitumor agents. VI. The isolation and structure of taxol, a novel antileukemic and antitumor agent from *Taxus brevifolia*. J. Am. Chem. Soc. 93:2325; 1971.
17. Wiernik, P. H. et al. Phase I clinical and pharmacokinetic study of taxol. Cancer Res. 47:2486; 1987.
18. Wiernik, P. H. et al. Phase I trial of taxol given as a 24-hour infusion every 21 days: responses observed in metastatic melanoma. J. Clin. Oncol. 5:1232; 1987.

This invention provides a method of increasing sensitivity of cells to cytotoxic effects of ionizing radiation which includes incubating the cells with spindle poison in suitable carrier at a concentration effective to inhibit the cells from progressing through G2 or M phases of the cell cycle for a time effective to inhibit division of the cells and then administering a cytotoxic dose of ionizing radiation to the cells. This invention also provides a method of treating a cancer patient which comprises administering to patient a spindle poison in suitable carrier in an amount effective to inhibit tumor cells in the patient from progressing through G2 or M phases of the cell cycle for an amount of time effective to inhibit division of the tumor cells and then administering a cytotoxic dose of ionizing radiation to the patient. This invention further provides a method for increasing the sensitivity of cells to bleomycin and a kit useful for treating cancer patients.

What is claimed is:

1. A method of increasing the sensitivity of cells to the cytotoxic effects of ionizing radiation which comprises first incubating the calls with a spindle poison in a suitable carrier at a concentration effective to inhibit the cells from progressing through the G2 or M phases of the cell cycle for an amount of time effective to inhibit division of the calls and then administering an effective cytotoxic dose of ionizing radiation to the cells.

2. The method of claim 1, wherein the cells are tumor cells.

3. The method of claim 2, wherein the tumor cells are brain tumor cells.

4. The method of claim 3, wherein the brain tumor cells are astrocytoma, glioblastoma multiformed or medulloblastoma cells.

5. The method of claim 2, wherein the tumor cells are ovarian tumor cells.

6. The method of claim 5, wherein the ovarian tumor cells are epithelial, sex-chord stromal, lipid, germ or gonadoblastoma cells.

7. The method of claim 2, wherein the tumor cells are lung tumor cells.

8. The method of claim 7, wherein the lung tumor cells are adenocarcinoma, large cell, small cell or squamous cell tumor cells.

9. The method of claim 2, wherein the tumor cells are breast tumor cells.

10. The method of claim 9, wherein the breast tumor cells are invasive duct carcinoma, medullary carcinoma or mucinous carcinoma cells.

11. The method of claim 2, wherein the tumor cells are melanoma cells.

12. The method of claim 1, wherein the spindle poison is a taxol-related compound.

13. The method of claim 12, wherein the taxol-related compound is taxol.

14. The method of claim 13, wherein taxol is a natural product of the yew Taxis Sp. L.

15. The method of claim 1, wherein the suitable carrier is an aqueous solution.

16. The method of claim 15, wherein the aqueous saline solution comprises dimethyl sulfoxide.

17. The method of claim 1, wherein the effective inhibiting concentration of the spindle poison is a concentration from about 1 nM to about 50 $\mu$M.

18. The method of claim 1, wherein the effective inhibiting amount of time is from about 6 hours to about 24 hours.

19. The method of claim 18, wherein the effective inhibiting amount of time is an amount from about 8 hours to about 20 hours.

20. The method of claim 19, wherein the effective inhibiting amount of time is an amount about 18 hours.

21. The method of claim 1, wherein an effective cytotoxic dose of ionizing radiation is administered to the cells by exposing the cells to a beam of radiation.

22. The method of claim 21, wherein the beam of radiation is produced by an irradiator.

23. The method of claim 22, wherein the irradiator comprises the radioisotope Cesium-137.

24. The method of claim 22, wherein the irradiator comprises the radioisotope Iridium-192.

25. The method of claim 1, wherein an effective cytotoxic dose of ionizing radiation is administered to the cells by contacting the cells with an aqueous solution containing a radioisotope.

26. The method of claim 25, wherein the radioisotope is Phosphorous-32.

27. The method of claim 21 or 25, wherein the effective cytotoxic dose of ionizing radiation is a dose from about 1 Gy to about 10 Gy.

28. The method of claim 27, wherein the effective cytotoxic dose of ionizing radiation is a dose from about 2 Gy to about 8 Gy.

* * * * *